United States Patent
Andrianov et al.

(10) Patent No.: US 10,076,573 B2
(45) Date of Patent: Sep. 18, 2018

(54) BIODEGRADABLE POLYPHOSPHAZENES CONTAINING PYRROLIDONE SIDE GROUPS

(71) Applicants: Alexander Andrianov, Gaithersburg, MD (US); Alexander Marin, Rockville, MD (US)

(72) Inventors: Alexander Andrianov, Gaithersburg, MD (US); Alexander Marin, Rockville, MD (US)

(73) Assignee: Innovo Biopolymers, LLC, Rockville, MD (US)

( * ) Notice: Subject to any disclaimer, the term of this patent is extended or adjusted under 35 U.S.C. 154(b) by 965 days.

(21) Appl. No.: 14/535,562

(22) Filed: Nov. 7, 2014

(65) Prior Publication Data

US 2015/0064106 A1 Mar. 5, 2015

Related U.S. Application Data

(63) Continuation of application No. 14/043,061, filed on Oct. 1, 2013, now Pat. No. 9,460,129, which is a continuation of application No. 13/470,453, filed on May 14, 2012, now abandoned, which is a continuation of application No. 12/803,908, filed on Jul. 9, 2010, now abandoned, which is a continuation of application No. 11/974,528, filed as application No. PCT/US2006/013661 on Apr. 11, 2006, now abandoned.

(60) Provisional application No. 60/672,191, filed on Apr. 15, 2005.

(51) Int. Cl.
*A61K 31/195* (2006.01)
*A61K 47/34* (2017.01)
*A61L 29/06* (2006.01)
*A61L 29/08* (2006.01)
*A61L 31/06* (2006.01)
*A61L 31/10* (2006.01)
*A61L 27/18* (2006.01)
*A61L 27/34* (2006.01)

(52) U.S. Cl.
CPC .............. *A61K 47/34* (2013.01); *A61L 27/18* (2013.01); *A61L 27/34* (2013.01); *A61L 29/06* (2013.01); *A61L 29/085* (2013.01); *A61L 31/06* (2013.01); *A61L 31/10* (2013.01)

(58) Field of Classification Search
USPC .......................................... 514/561; 424/423
See application file for complete search history.

(56) References Cited

PUBLICATIONS

Andrianov et al., Macromolecules, 2005, 38:7972-7976.*

* cited by examiner

*Primary Examiner* — Rei Tsang Shiao
(74) *Attorney, Agent, or Firm* — Raymond J. Lilllie (57) ABSTRACT

Biodegradable polyphosphazene polymers containing pyrrolidone side groups, and the biomedical use of such polyphosphazene polymers are disclosed.

18 Claims, 6 Drawing Sheets

BIODEGRADABLE POLYPHOSPHAZENES CONTAINING PYRROLIDONE SIDE GROUPS

CROSS-REFERENCE TO RELATED APPLICATIONS

This application is a continuation of application Ser. No. 14/043,161 filed Oct. 1, 2013, which is a continuation of Ser. No. 13/470,453, filed May 14, 2012, which is a continuation of application Ser. No. 12/803,908, filed Jul. 9, 2010, which is a continuation of application Ser. No. 11/974,528, filed Oct. 12, 2007, abandoned, which is a continuation of application Ser. No. 10/715,787, filed Nov. 18, 2003, abandoned, which claims priority based on provisional application Ser. No. 60/428,426, filed Nov. 22, 2002, the contents of which are incorporated by reference in their entireties.

DETAILED DESCRIPTION OF THE INVENTION

This invention relates to polyphosphazenes containing pyrrolidone side groups. Such polymers can be particularly useful as drug delivery carriers, plasma expanders, and biocompatible coatings for medical devices.

Polyphosphazenes are polymers with backbones including alternating phosphorus and nitrogen atoms, separated by alternating single and double bonds. Each phosphorous atom is covalently bonded to two pendant groups ("A").

The repeat unit of a polyphosphazene has the following formula:

wherein each "A" may be the same, or different, and wherein the unit is repeated "n" times.

When the polyphosphazene has only one type of pendant group or side group repeatedly attached to its backbone the polymer is said to be a homopolymer. When the polyphosphazene has more than one type of pendant group, the polyphosphazene is a copolymer. When the groups vary randomly throughout the polymer, the polyphosphazene is a random copolymer. Phosphorous can be bound to two like groups, or to two different groups.

Polyphosphazenes with desired side groups can be produced by initially producing a reactive macromolecular precursor—poly(dichlorophosphazene) and then by reacting it with a nucleophile that contains the desired side group, such nucleophiles include alcohols, amines, or thiols. Polyphosphazenes with two or more types of pendant groups can be produced by reacting poly(dichlorophosphazene) with two or more types of nucleophiles in a desired ratio. Nucleophiles can be added to the reaction mixture simultaneously or in sequential order. The resulting ratio of pendant groups in the polyphosphazene will be determined by a number of factors, including the ratio of starting materials used to produce the polymer, the order of addition, the temperature at which the nucleophilic substitution reaction is carried out, and the solvent system used. The ratio of groups in the polymer can be easily determined by one skilled in the art.

The polymers of the present invention may be produced by reacting poly(dichlorophosphazene) with an organic nucleophile containing a pyrrolidone moiety. For example, an organic compound containing hydroxyl group and N-alkyl pyrrolidone may be reacted with the reactive chlorine atoms on poly(dichlorophosphazene). One or a mixture of organic compounds can be used to result in a homopolymer or mixed substituent copolymers correspondingly. Hydroxyl group of the organic compound can be activated with sodium, sodium hydride, or sodium hydroxide by procedures known in the art and then reacted with chlorine atoms attached to the polyphosphazene backbone.

Thus, in one aspect, the present invention provides a polyphosphazene polymer that contains repeating units of the following formula:

wherein in each monomeric unit of the polymer, each R is the same or different, and wherein at least a portion of the monomeric units of the polymer one or more of the R groups is "X." Wherein "X" is:

wherein Z is oxyalkyl; oxyarylalkyl; oxyaryl; aminoalkyl; aminoarylalkyl; aminoaryl; thioalkyl; -thioarylalkyl; thioaryl; aryl; arylalkyl; aryl.

The remaining R groups may be one or more of a wide variety of substituent groups. As representative, non-limiting examples of such groups there may be mentioned: aliphatic; aryl; aralkyl; alkaryl; carboxylic acid; heteroaromatic; carbohydrates, including glucose; heteroalkyl; halogen; (aliphatic)amino- including alkylamino-; heteroaralkyl; di(aliphatic)amino- including dialkylamino-, arylamino-, diarylamino-, alkylarylamino-; -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic)PO$_3$H, and -oxy(aliphatic)hydroxyl, including oxy(alkyl)hydroxyl; -oxyalkaryl; -oxyaralkyl; -thioaryl; aminoacid, aminoacid ester, thioaliphatic including -thioalkyl; -thioalkaryl; thioaralkyl; —NHC(O)O-(aryl or aliphatic); —O—[(CH$_2$)$_x$O]$_y$—CH$_2$—O—[(CH$_2$)$_x$O]$_y$(CH$_2$)$_x$NH(CH$_2$)$_x$SO$_3$H; and —O—[(CH$_2$)$_x$O]$_y$-(aryl or aliphatic); wherein x is 1-8 and y is an integer of 1 to 20. The remaining R groups can be immunostimulating carboxylic acid containing groups. The groups can be bonded to the phosphorous atom through, for example, an oxygen, sulfur, nitrogen, or carbon atom.

It is an aspect of the instant invention that the polyphosphazene polymer as hereinabove described and as hereinbelow described has an overall molecular weight of 1,000 g./mol. to 10,000,000 g./mol.

Polyphosphazenes of the present invention can be homopolymers, having one type of side groups, or mixed substituent copolymers, having two or more types of side groups.

The preferred polymer of the present invention contains N-ethyl pyrrolidone group:

A particularly preferred polymer of the present invention is poly {di[2-(2-oxo-1-pyrrolidinyl)ethoxy]phosphazene} or poly{di[2-(1-pyrrolid-2-one)ethoxy]phosphazene}, PYRP:

wherein n is a number that provides the desired molecular weight. For example, n may be from 10 to 10,000.

In mixed substituent copolymers there is at least one type of side group that contains pyrrolidone functionality and one type of side groups that does not contain pyrrolidone functionality. Side groups that do not contain pyrrolidone functionalities can be introduced in a polyphosphazene copolymer to modulate physical or physico-chemical properties of the polymer. Such side groups can be used, for example, to modulate water-solubility, biodegradability, hydrophobicity, or to make them biologically active. As non-limiting examples of such non-pyrrolidone functionality containing physical or physico-chemical property modulating side groups there may be mentioned side groups that include amino acids and their esters, carboxylic acids, phenoxy, alkoxy, hydroxy, halogen, and methoxyethoxyethoxy.

In a co-polymer, in general, the side groups that contain a pyrrolidone functionality comprise from 0.5% to 99.5% of the total side groups and preferably at least 10% of the total side groups.

An example of mixed substituent copolymers is the following:

The polyphosphazenes of the present invention are polymers that are preferably biodegradable when administered to either humans or animals. Biodegradability of the polymer prevents eventual deposition and accumulation of polymer molecules at distant sites in the body, such as the spleen. The term biodegradable, as used herein, means a polymer that degrades within a period that is acceptable in the desired application, typically less than about five years and most preferably less than about one year.

The polyphosphazenes of the present invention are polymers that are preferably biocompatible. "Biocompatible material" may be defined as a polymer that is designed and constructed to be placed in or onto the body or to contact fluid or tissue of the body. Ideally, a biocompatible polymer will not induce undesirable reactions in the body such as blood clotting, tissue death, tumor formation, allergic reaction, foreign body reaction (rejection) or inflammatory reaction; will have the physical or biological properties required to function for the intended purpose; can be purified, fabricated, and sterilized easily; and will substantially maintain its function during the time that it remains in contact with the body.

The polyphosphazenes of the present inventions can be used in the water-soluble form or as solid materials.

They may be used in controlled release formulations and can be dissolved and/or suspended in water or any other suitable liquid medium in which the polymers are soluble and/or dispersible and combined with a pharmacological or pharmaceutical compound or composition to form a composition of matter. The polymer will act as a matrix for the pharmaceutical to provide an article of manufacture for the controlled release of such pharmaceutical. It can stabilize and protect the pharmaceutical. The pharmaceuticals can be attached to the polymer covalently or they can be associated with the polymer through non-covalent linkages, such as ionic, hydrogen bonds, or hydrophobic interactions.

The polymers may be used for the encapsulation of pharmaceutical agents to produce microspheres, microcapsules, micelles, or the polymers may be used to stabilize liposomes.

Pharmaceuticals which may be included in the resulting article of manufacture are listed in the Physicians' Desk Reference, 57th Edition (2003), and include allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, anti-migraine preparations, antinauseants, antineoplastics, anti-obesity preparations, antiparasitics, anti-parkinsonism drugs, antipruritics, antipyretics, antispasmodics and anticholinergics, antitoxoplasmos is agents, antitussives, antivertigo agents, antiviral agents, biologicals, bismuth preparations, bone metabolism regulators, bowel evacuants, bronchial dilators, calcium preparations, cardiovascular preparations, central nervous system stimulants, cenimenolytics, chelating agents, choleretics, cholesterol reducers and anti-hyperlipemics, colonic content acidifiers, cough and cold preparations, decongestants, expectorants and combinations, diuretics, emetics, enzymes and digestants, fertility agents, fluorine preparations, galactokinetic agents, geriatrics, germicides, hematinics, hemorrhoidal preparations, histamine H. receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the Physicians' Desk Reference, (supra).

The polymers of the present invention are used in an amount sufficient to form a matrix around the composition or material to be released in the time release formulations or to act as a carrier for such compositions or materials in such formulations and can be employed in an amount sufficient to permit the delayed time release of a composition or material into its environment, e.g., anywhere from about 1% by weight to about 99% by weight of the time release formulation and preferably from about 5% by weight to about 99% by weight of the time release formulation.

Polymers of the present invention can be used as coatings or materials for "medical devices"—articles that have surfaces that contact blood or other bodily tissues in the course of their operation. This can include, for example, extracorporeal devices for use in surgery such as blood oxygenators, blood pumps, blood sensors, tubing used to carry blood, and the like, which contact blood, which is then returned to the patient. This can also include implantable devices such as vascular grafts, stents, electrical stimulation leads, heart valves, orthopedic devices, catheters, guide wires, shunts, sensors, replacement devices for nucleus pulposus, cochlear or middle ear implants, intraocular lenses, and the like. Coatings or materials for medical devices can be designed to release drugs for an extended period of time.

The polyphosphazene polymers of the present invention may be used as coating agents for the construction of monolayer and multilayer assemblies. Such assemblies are constructed by layer-by-layer polyelectrolyte deposition. This includes direct adsorption of polyelectrolytes onto suitable solids, at the interface between the solid and a fluid phase containing the monolayer forming molecules. The process can be continued until the targeted number of monolayers, one upon the other, is obtained (U.S. Pat. No. 4,539,061). Typically, a multilayer coating can contain 5 to 20 layers of polyelectrolytic materials. Desired functional groups can be included at the upper surface of the coating to obtain a surface with a required set of properties. Multilayer coatings can be used in a wide range of industrial applications, such as but not limited to, preparation of artificial membranes, fabrication of passive and active ultrathin film components for novel microelectronic and optical devices, ultrathin photoresists, and molecular films useful in solar energy conversion, etc. Multilayer coatings can be used in biomedical devices. Biomedical devices include a wide variety of devices used in the biological, medical, or personal care industries and include, but are not limited to, ophthalmic lenses, drug delivery devices such as oral osmotic devices and transdermal devices, catheters, contact lens disinfection and cleaning containers, breast implants, stents, intervertebral discs, artificial organs and tissues, and the like. Many devices and materials used in biomedical applications require certain properties in the bulk of the device or material with distinct and separate properties required for the surface. For example, a contact lens may have a core or bulk material which is highly oxygen permeable and hydrophobic, and a surface which has been treated or coated to increase the hydrophilicity, thereby allowing the lens to move freely on the eye. Other biomaterials require coatings effective in preventing protein adsorption on biosurfaces and preventing fouling.

The invention now will be described with respect to the following examples; it is to be understood, however, that the scope of the present invention is not intended to be limited thereby.

Example 1. Synthesis of Poly{di[2-(2-oxo-1-pyrrolidinyl)ethoxy]phosphazene}, PYRP A suspension of sodium hydride (0.066 g; 0.0026 mol) in 1,4-dioxane (0.0008 L) was slowly added to 1-(2-hydroxyethyl) pyrrolidone (1.59 g; 0.0123 mol) in 1,4-dioxane (0.010 L) under nitrogen to form sodium 1-(2-hydroxyethyl) pyrrolidone. This solution was diluted with 0.015 L of 1,4-dioxane, and then heated to 50° C. with stirring under dry nitrogen. 0.002 L of polydichlorophosphazene (0.116 g; 0.001 moles) was then added slowly via syringe over a period of five minutes. The reaction mixture was stirred for fifteen hours at 50° C., then cooled to ambient temperature and precipitated with hexane. The precipitate was collected by decantation, dried under vacuum, and then dissolved in water. The polymer then was purified using a Biocad Perfusion Chromatography Workstation (Applied Biosystems, Foster Hills, Calif.) equipped with a Modcol CER 3662 column using 0.02 M ammonium bicarbonate. Polymer fractions were collected and then lyophilized. The yield was 0.113 g (37.5% of theoretical). Polymer structure was confirmed by $^1$H NMR, $^{13}$C NMR and $^{31}$P NMR (Table 1) and molecular weight was determined by GPC-light scattering and GPC using poly(ethylene oxide) standards (Table 2).

Example 2. Synthesis of Poly{[2-(2-oxo-1-pyrrolidinyl)ethoxy](4-carboxylatophenoxy)phosphazenel} (CP1)

A suspension of sodium hydride (0.086 g; 0.003 moles) in 1,4-dioxane (0.002 L) was slowly added to a solution of 1-(2-hydroxyethyl) pyrrolidone (2.08 g; 0.016 moles) in 0.010 L of 1,4-dioxane under nitrogen to form sodium 1-(2-hydroxyethyl) pyrrolidone. Sodium propyl 4-hydroxybenzoate was prepared by adding a suspension of sodium hydride (0.61 g; 0.025 moles) in diglyme (0.004 L) to a solution of propyl ester of 4-hydroxybenzoic acid (5.19 g; 0.029 moles) in 0.010 L diglyme under dry nitrogen. 0.0005 L of the sodium propyl 4-hydroxybenzoate solution was added to the sodium 1-(2-hydroxyethyl) pyrrolidone solution at ambient temperature.

0.002 L of polydichlorophosphazene (0.116 g; 0.001 moles) was then added slowly at room temperature over a period of five minutes. Following the addition, the temperature was raised to 50° C., and stirred for fifteen hours. 0.001 L of 12.7 N aqueous potassium hydroxide solution was slowly added, and the reaction mixture was stirred for one hour at 50° C.

The precipitate was collected by decantation, dried and dissolved in water. The polymer then was purified chromatographically as described above. The yield of polymer (CP1) was 0.228 g (75% of theoretical). Polymer characterization data is presented in Tables 1 and 2.

The composition of mixed substituent polymer was determined using two methods. (1) It was calculated based on the ratio between the peak areas of ethylene protons of the ethylpyrrolidone side group and the aromatic protons of the carboxylatophenoxy side group in 1H NMR. (2) The composition was established using HPLC based on the differences in the UV absorbance of PCPP and PYRP at 254 nm in PBS (pH 7.4). Calibration curves were obtained for the mixtures of PCPP and PYRP by plotting HPLC peak areas at 254 nm versus mixture composition. The total polymer

TABLE 1

NMR characterization data.

| Polymer | NMR, ppm |
|---|---|
| PYRP | $^1$H 2.02 (d); 2.38 (e); 3.49 (b); 3.51 (c); 4.03 (a)<br>$^{13}$C 178.11 (f); 63.65 (a); 48.61 (b); 43.11 (c); 30.79 (e); 17.78 (d)<br>$^{31}$P −7.4 |
| CP1:CP2 | $^1$H 1.97 (d); 2.37 (e); 3.41 (b); 3.47 (c); 3.95 (a); 7.25 (h); 7.94 (g)<br>$^{31}$P −19.7; −13.7; −7.4. |

TABLE 2

Polymer compositions and molecular weights.

| Polymer | Composition, x:y | | | $M_w$, g/mol × 10$^{-3}$ | | |
|---|---|---|---|---|---|---|
| | Expected * | $^1$H NMR | UV-HPLC | MALLS-GPC # | GPC (PEO) $^\Delta$ | |
| PYRP | 2:0 | 2:0 | 2:0 | 370 | 305 | |
| CP1 | 1.70:0.30 | 1.70:0.30 | 1.64:0.36 | 1000 | 610 | |
| CP2 | 0.3:1.70 | 0.18:1.82 | 0.18:1.82 | 513 | 471 | |

* based on the composition of the reaction mixture
based on GPC with multi angle laser light scattering detection
$^\Delta$ based on GPC with PEO standards concentration was maintained at 1 mg/mL and the results were processed using Millenium (Waters, Milford, Mass.) software. A copolymer was then analyzed by HPLC using the same conditions and its molar composition was determined using calibration curves obtained for the mixtures of homopolymers. Polymer composition data is presented in Table 2.

Example 3. Synthesis of Poly{[2-(2-oxo-1-pyrrolidinyl)ethoxy](4-carboxylatophenoxy)phosphazene} (CP2)

A suspension of sodium hydride (0.247 g; 0.0098 moles) in 1,4-dioxane (0.105 L) was slowly added to 1-(2-hydroxyethyl)-2-pyrrolidone (5.989 g; 0.0464 moles) in 1,4-dioxane (0.025 L) under a dry nitrogen to form a sodium 1-(2-hydroxyethyl)-2-pyrrolidone solution. Sodium propyl 4-hydroxybenzoate was prepared by adding a suspension of sodium hydride (0.707 g; 0.0279 moles) in diglyme (0.003 L) to 4-hydroxybenzoate propyl ester (6.055 g; 0.3360 moles) in diglyme (0.010 L) under a dry nitrogen atmosphere. 0.003 L polydichlorophosphazene (0.232 g; 0.002 moles) was diluted with 0.013 L diglyme at room temperature under nitrogen and then heated to 50° C. 0.0024 L of the sodium propyl 4-hydroxybenzoate was added while stirring. The temperature was increased to 100° C., the reaction mixture was stirred for three hours and then cooled to 50° C. To this 0.015 L of the sodium 1-(2-hydroxyethyl)-2-pyrrolidone solution was slowly added and the reaction continued for twenty hours. 0.010 L of 12.7 N potassium hydroxide solution was slowly added, and stirred for one hour at 50° C. The precipitated polymer was collected, dissolved in distilled water, and precipitated by adding 1 N hydrochloric acid until pH 3. The precipitate was re-dissolved in 0.05 M of ammonium bicarbonate and purified by preparative HPLC as described above. The yield of polymer (CP2) was 0.29 g (38.6% of theoretical). Polymer composition was determined as described in Example 2. Characterization data is presented in Tables 1 and 2.

Example 4. Polymer Degradation Studies

Solutions of polymers PYRP, CP1, CP2, and PCPP were prepared at a concentration of 1 mg/mL in the following buffers: citrate buffer, pH 3.0 (0.040 M citric acid; 0.021M sodium hydroxide; 0.060 M sodium chloride), Tris buffer, pH 7.4 (0.020 M Tris, 0.9% NaCl) and borate buffer, pH 9.3 (0.02 M sodium tetraborate). Samples were incubated at room temperature for 1 hour upon shaking to assure complete dissolution and then filtered using 0.45 µm Millex-HV syringe filters (Millipore, Bedford, Mass.).

Degradation studies were performed at 55° C. Vials containing polymer solutions were incubated in a G24 Environmental Incubator Shaker (New Brunswick Scientific, Edison, N.J.). 0.2 mL samples were collected periodically for the determination of molecular weight and degradation products. Analysis was conducted using size exclusion HPLC with triple detection system-multi-angle laser light scattering (DAWN DSP-F Wyatt Technology, Santa Barbara, Calif.), Waters 996 photo-diode array, and Waters 410 refractive index (Waters, Milford, Mass.). Absolute molecular weight parameters were determined using light scattering detection, refractive index detector as a mass detector, and ASTRA 2.1 software (Wyatt Technology, Santa Barbara, Calif.). Relative molecular weight characteristics were calculated based on calibration curves for poly(ethylene oxide) standards using photo-diode array detection with absorbance measured at 230 nm. Concentration of hydroxybenzoic acid (HBA) was determined by HPLC with UV detection at 280 nm using Millenium (Waters, Milford, Mass.) software. Phosphate buffered saline PBS, pH 7.4 was used as a mobile phase with a flow rate of 0.75 ml/min and injection volume of 0.1 mL.

Figure 1:
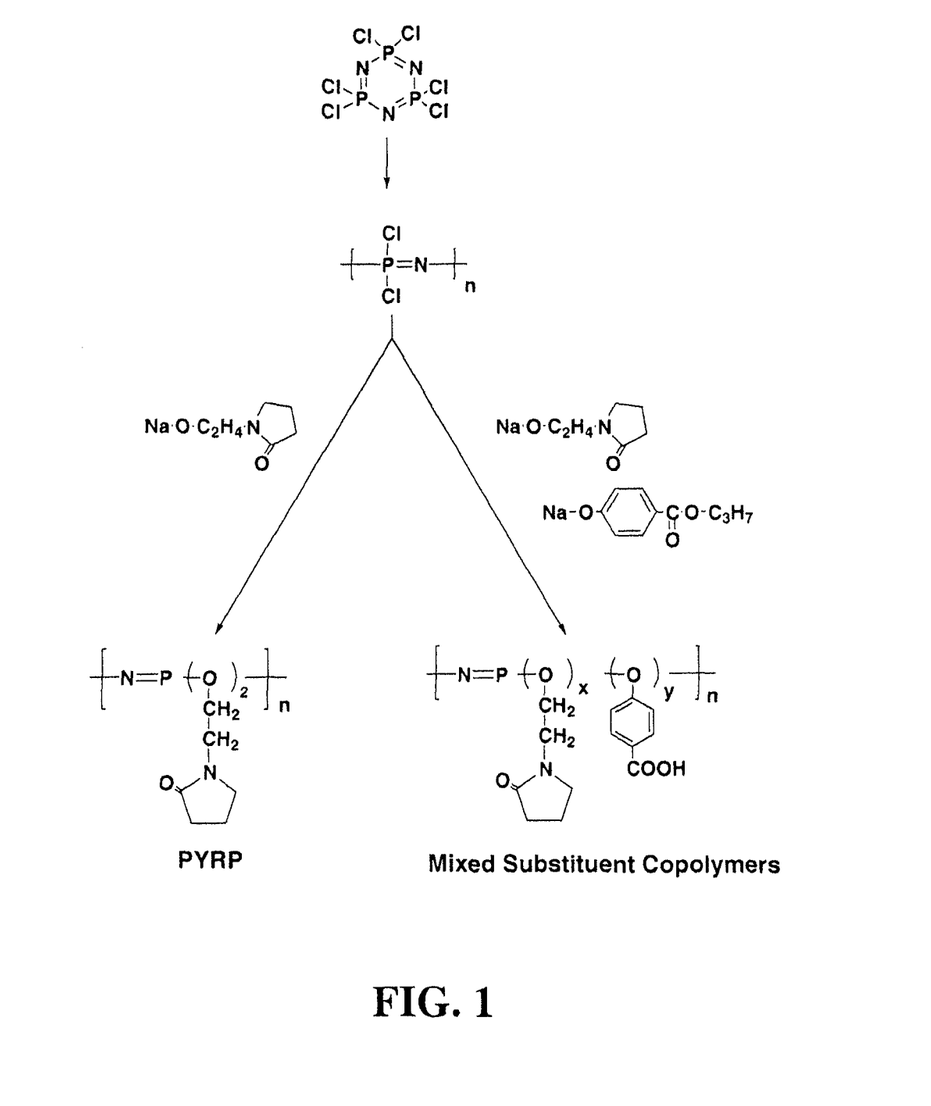
FIG. 1 represents a synthetic pathway to polyphosphazenes with N-alkyl pyrrolidone side groups.
Figure 2:
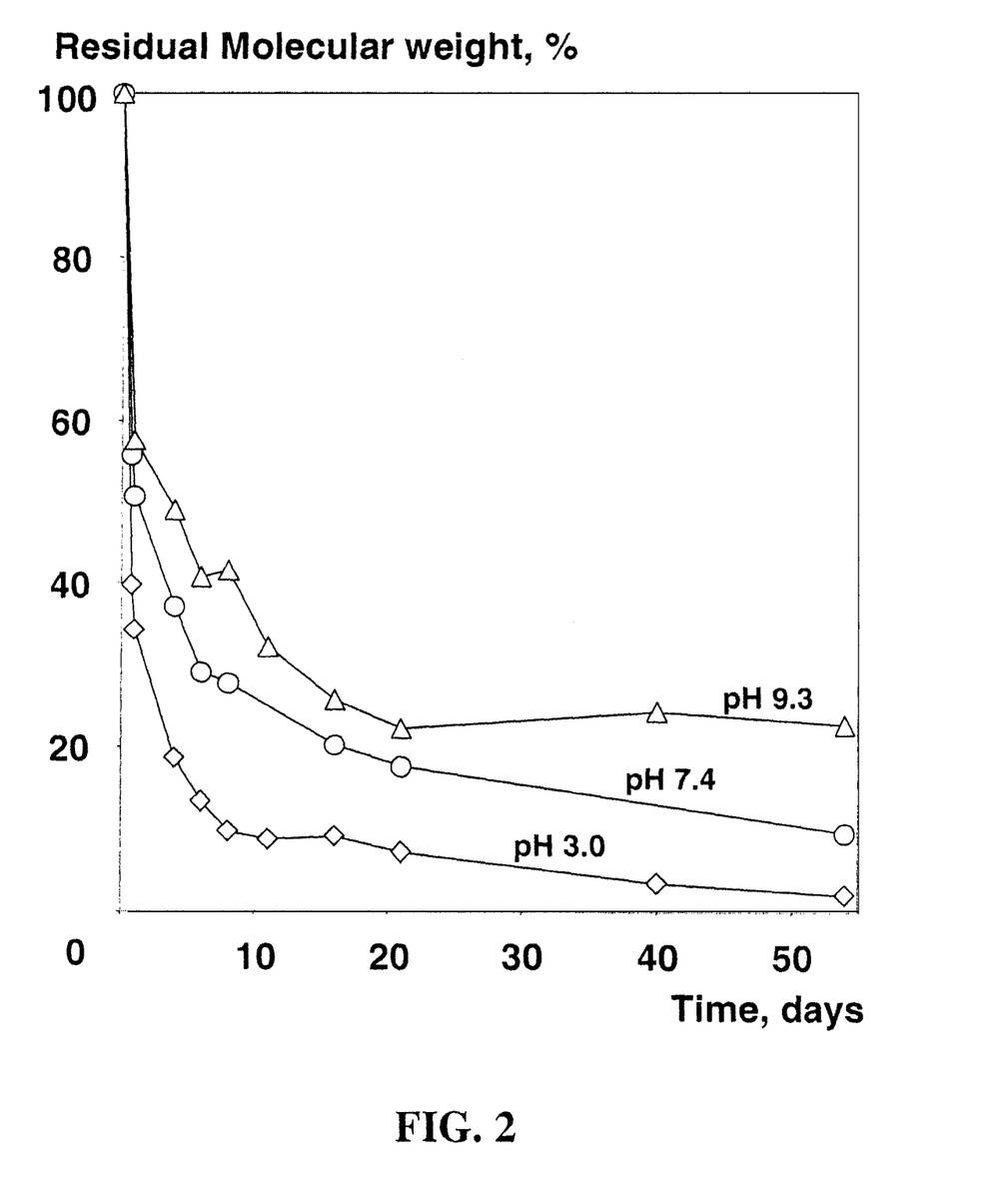
FIG. 2 represents molecular weight loss of the PYRP in aqueous solutions at various pH versus time (weight average molecular weight determined by light scattering, 55° C., 1 mg/mL).
Figure 3:
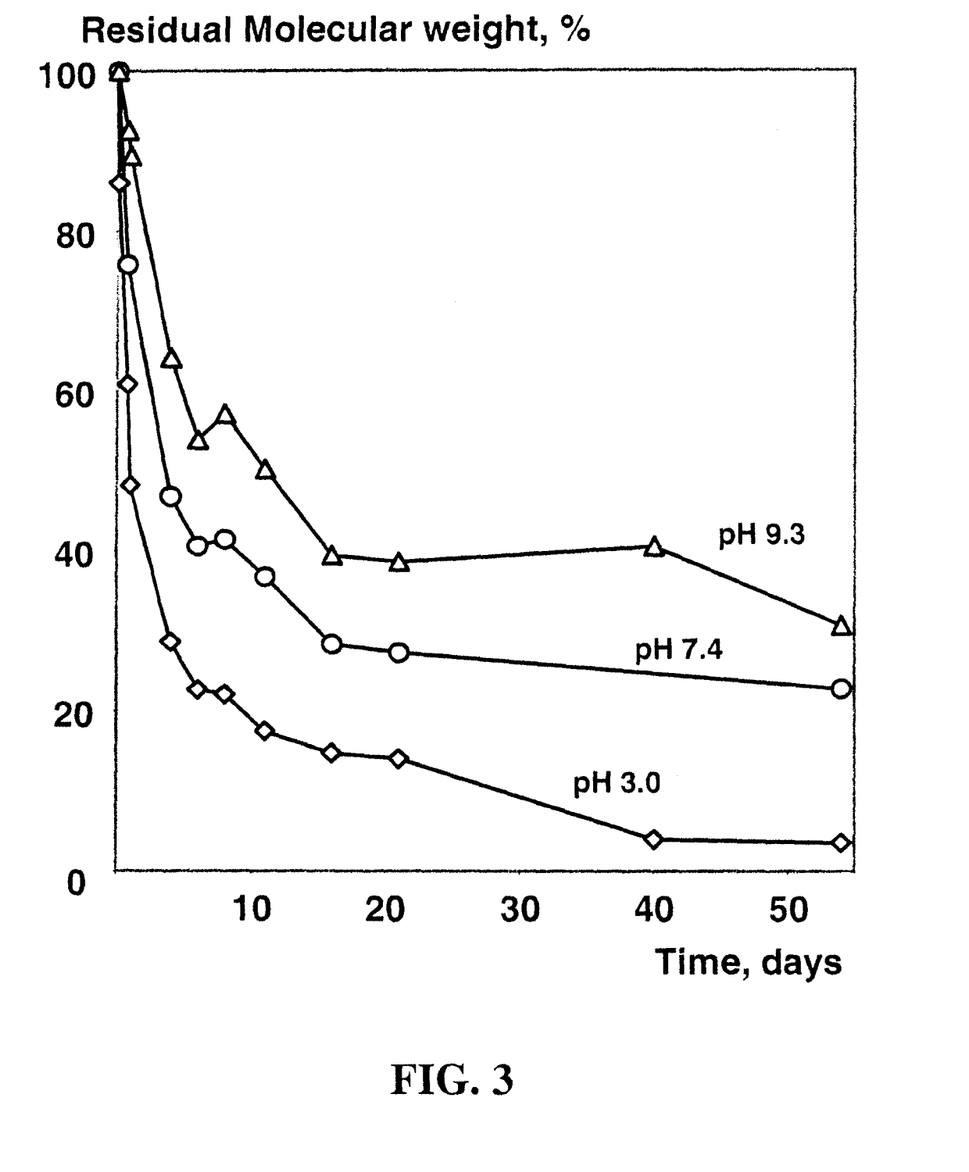
FIG. 3 represents molecular weight loss of the PYRP in aqueous solutions at various pH versus time (weight average molecular weight determined by GPC with PEO standards, 55° C., 1 mg/mL).
Figure 4:
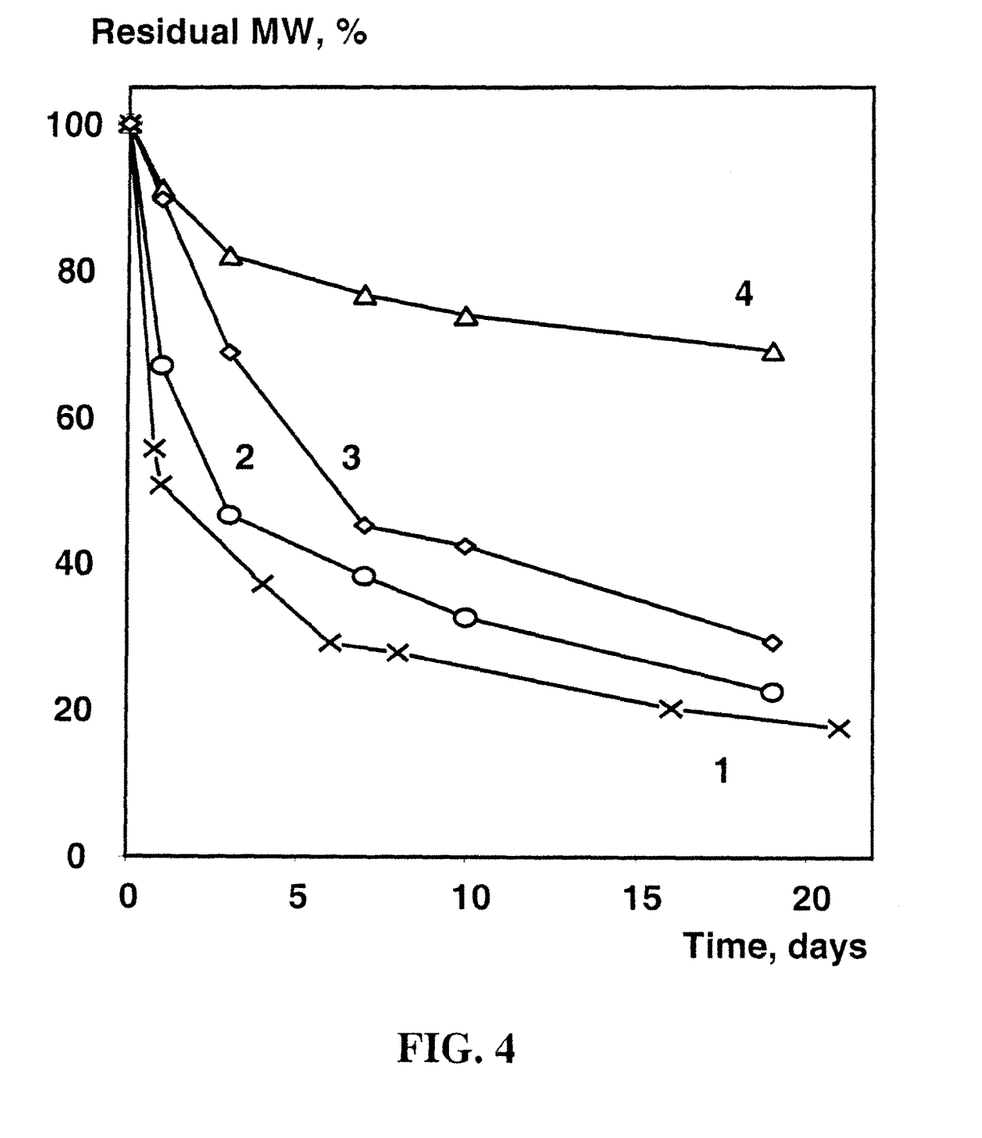
FIG. 4 represents molecular weight loss of the PYRP (1), CP1 (2), CP2 (3), and PCPP (4) in aqueous solutions versus time (weight average molecular weight determined by light scattering, 55° C., 1 mg/mL).
Figure 5:
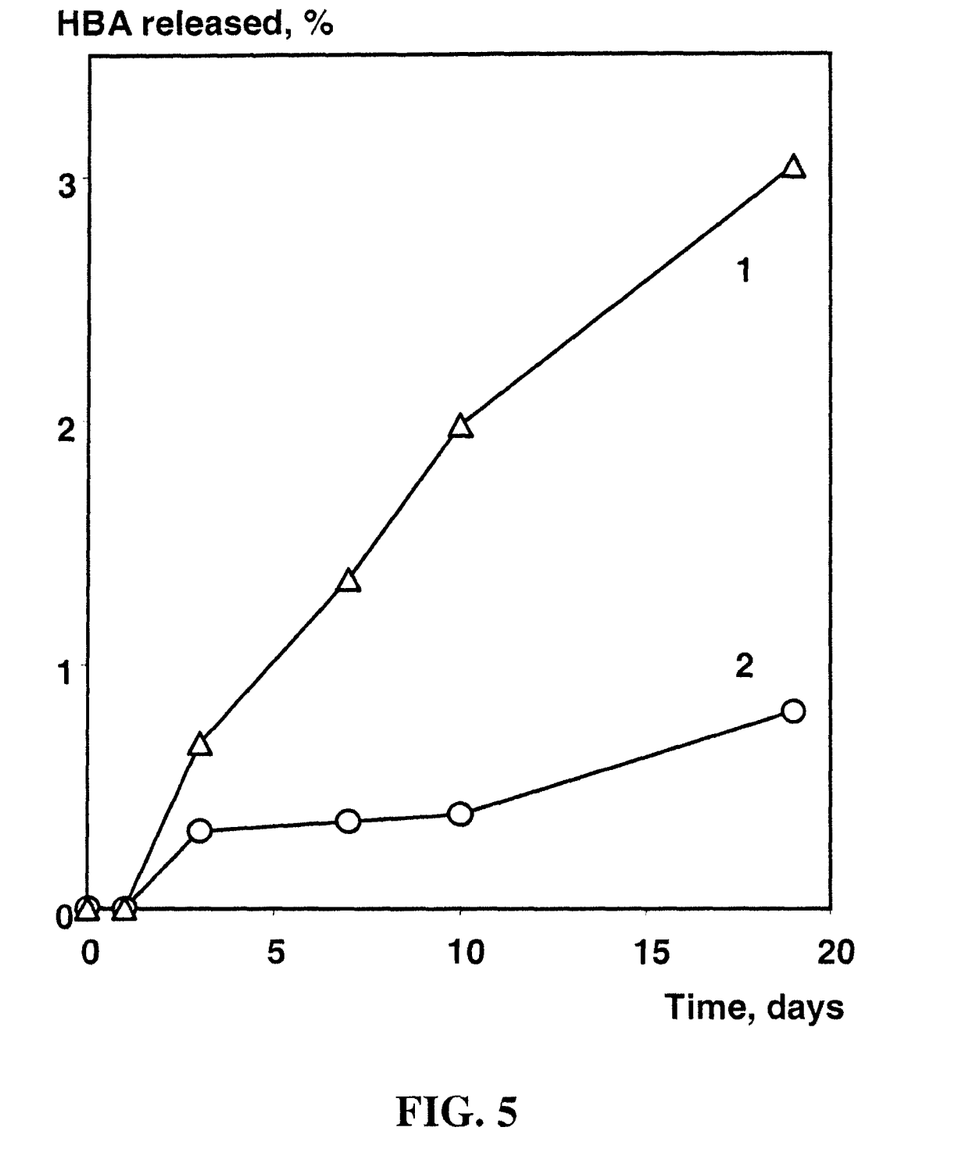
FIG. 5 represents release of p-hydroxybenzoic acid in aqueous solutions for CP1 (1) and PCPP (2) versus time (55° C., 1 mg/mL).

FIGS. 2-3 show the kinetics of weight average molecular weight decrease of PYRP in aqueous solutions with pH 9.3, pH 7.4, and pH 3.0 at 55° C. It appears that the rate of hydrolysis is pH dependent with the degradation rate increasing as pH declines. This relationship is observed for both, absolute molecular weight, determined by GPC with multi-angle laser light scattering detector (FIG. 2), and relative molecular weight, measured by GPC using PEO standards (FIG. 3). FIG. 4 shows degradation profiles for polymers PYRP, CP1, CP2, and PCPP in PBS, pH 7.4. Pyrrolidone containing homopolymer PYRP demonstrated the highest hydrolysis rate, and PCPP the lowest. Introduction of pyrrolidone side groups in the PCPP structure (CP1, CP2) resulted in a pronounced increase in the rate of molecular weight loss. The degradation of PCPP and its copolymer containing pyrrolidone groups (CP1) was also accompanied with a side group cleavage, manifested in the release of hydroxybenzoic acid (FIG. 5). Interestingly, the rate of release was higher for a copolymer CP1, which confirms a destabilizing effect of pyrrolidone side groups. Therefore, the ethylpyrrolidone moiety modulated polyphosphazene degradation.

Figure 6:
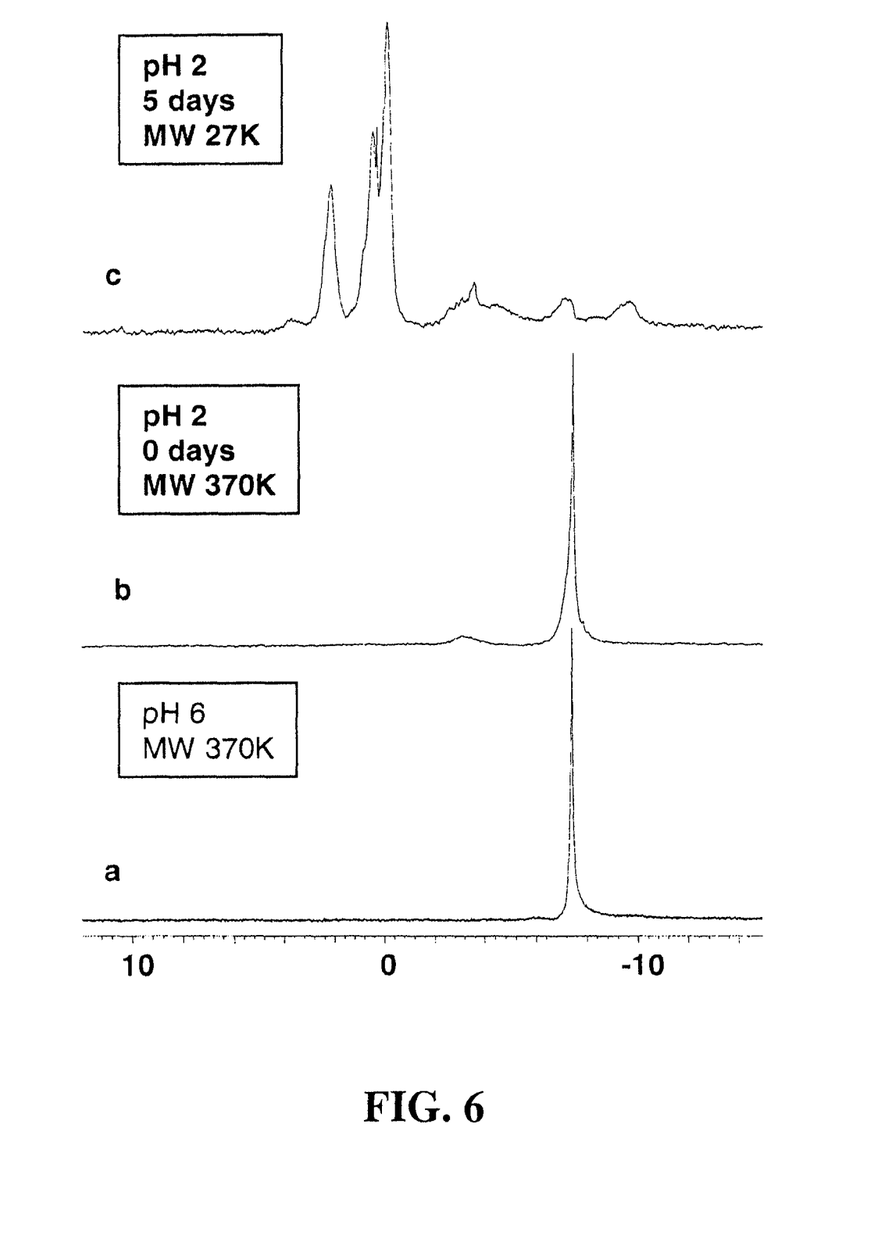
FIG. 6 represents $^{31}$P NMR spectra of PYRP in $D_2O$, pH 6 (a), in $D_2O$ after addition of deuterated hydrochloric acid, pH 2 (b), and after incubation of PYRP in $D_2O$—deuterated hydrochloric acid, pH 2 at 55° C. for 5 days (c). Molecular weights, determined by light scattering were 370,000 g/mol (a, b) and 27,000 g/mol (c).

FIG. 6 shows changes in the $^{31}$P NMR spectra observed during the hydrolysis of polymer PYRP in the acidic aqueous environment. Reaction of the polymer with water under acidic conditions proceeded rapidly enough so that additional peaks appeared immediately after admixing of the hydrochloric acid (FIG. 6b). Peak at -3.2 ppm can be ascribed to PPyrO; signals and -9.8, -7.8 and -8.0 can be assigned to α, β and γ PyrO—P—OPyr. Dramatic change in the ratio between the initial polymer peak PyrO—P—OPyr at -7.4 and α PyrO—P—OPyr peak, as the hydrolysis proceeds, supports this assumption. Peaks in the range of -1 to 4 ppm can be probably associated with low molecular weight phosphates, oligomers, and products of geminal hydrolysis.

$^1$H NMR analysis of the polymer hydrolyzed in the acidic solution for 5 days still showed original peaks macromolecular peaks of PYRP, which was expected since light scattering analysis demonstrated the presence of polymer with the molecular weight of 27,000 g/mol. In addition N-ethyl pyrrolidone peaks were present, indicating the release of the side group from the polymer. The amount of the low molecular weight compound in the system was estimated to be approximately 70% of the total of N-alkyl pyrrolidone that can be released from the polymer. No other compounds were detected in the system demonstrating the absence of ring opening reactions.

What is claimed is:
1. A polyphosphazene polymer having the following units:

wherein at least one R has the formula:

wherein Z is oxyalkyl; oxyarylalkyl; oxyaryl; aminoalkyl; aminoarylalkyl; aminoaryl; thioalkyl; -thioarylalkyl; thioaryl; aryl; or arylalkyl.

2. The polyphosphazene polymer of claim 1 wherein Z is oxyethyl, and said polyphosphazene polymer has the following structural formula:

and wherein n is from 10 to 10,000.

3. The polyphosphazene polymer of claim 1, wherein at least one R group is selected from the group consisting of: aliphatic; aryl; aralkyl; alkaryl; carboxylic acid; heteroaromatic; carbohydrates, including glucose; heteroalkyl; halogen; (aliphatic)amino- including alkylamino-; heteroaralkyl; di(aliphatic)amino- including dialkylamino-, arylamino-, diarylamino-, alkylarylamino-; -oxyaryl including but not limited to -oxyphenyl$CO_2$H, -oxyphenyl$SO_3$H, -oxyphenylhydroxyl and -oxyphenyl$PO_3$H; -oxyaliphatic including -oxyalkyl, -oxy(aliphatic)$CO_2$H, -oxy(aliphatic)$SO_3$H, -oxy(aliphatic)$PO_3$H, and -oxy(aliphatic)hydroxyl, including oxy(alkyl)hydroxyl; -oxyalkaryl, -oxyaralkyl; -thioaryl; aminoacid, aminoacid ester, thioaliphatic including -thioalkyl; -thioalkaryl; thioaralkyl; —NHC(O)O-(aryl or aliphatic); —O—[$(CH_2)_xO]_y$—$CH_2$)—O—[$(CH_2)_xO]_y(CH_2)_x$NH$(CH_2)_x$SO$_3$H; and —O—[$(CH_2)_xO]_y$-(aryl or aliphatic); wherein x is 1-8 and y is an integer of 1 to 20.

4. The polyphosphazene polymer of claim 1, having a molecular weight of 1,000 g/mol. to 10,000,000 g./mol.

5. The polyphosphazene polymer of claim 1, in the form of a homopolymer.

6. The polyphosphazene polymer of claim 1, in the form of a copolymer.

7. The polyphosphazene copolymer of claim 6, wherein said copolymer has side groups that contain a pyrrolidone functionality, and wherein the side groups that contain a pyrrolidone functionality comprise from 0.5% to 99.5% of the total side groups.

8. The polyphosphazene copolymer of claim 7, wherein the side groups that contain a pyrrolidone functionality comprise at least 10% of the total side groups.

9. A pharmaceutical composition comprising a pharmaceutically active agent and a carrier for providing controlled release of said pharmaceutically active agent, said carrier comprising the polyphosphazene polymer of claim 1.

10. The pharmaceutical composition of claim 9, wherein said carrier is in a form selected from the group consisting of: matrices, microspheres, microcapsules, micelles, and stabilized liposomes.

11. The pharmaceutical composition of claim 9, wherein said polyphosphazene polymer comprises about 1% by weight to about 99% by weight of said carrier for providing controlled release of said pharmaceutically active agent.

12. The pharmaceutical composition of claim 11, wherein said polyphosphazene polymer comprises about 5% by weight to about 99% by weight of said carrier for providing controlled release of said pharmaceutically active agent.

13. The pharmaceutical composition of claim 9, wherein said pharmaceutically active agent is selected from the group consisting of: allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, anti-migraine preparations, antinauseants, antineoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, expectorants and combinations, diuretics, emetics, enzymes and digestants, fertility agents, fluorine preparations, galactokinetic agents, geriatrics, germicides, hematinics, hemorrhoidal preparations, histamine H. receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics, and vitamins.

14. A Poly{di[2-(2-oxo-1-pyrrolidinyl)ethoxy]phosphazene} having the following structural formula:

wherein each of a, b, c, d, e, and f are NMR data characterizing said Poly{di[2-(2-oxo-1-pyrrolidinyl)ethoxy]phosphazene} as follows:

| NMR, ppm | |
|---|---|
| $^1$H | 2.02 (d); 2.38 (e); 3.49 (b); 3.51 (c); 4.03 (a) |
| $^{13}$C | 178.11 (f); 63.65 (a); 48.61 (b); 43.11 (c); 30.79 (e); 17.78 (d) |
| $^{31}$P | −7.4. | and wherein n is from 10 to 10,000.

15. An extracoporeal device for use in surgery, comprising coatings or materials comprising the polyphosphazene polymer of claim 1.

16. The extracoporeal device of claim 15, in a form selected from the group consisting of: blood oxygenators, blood pumps, blood sensors, and tubing used to carry blood.

17. A surgically implantable device, comprising coatings or materials comprising the polyphosphazene polymer of claim 1.

18. The surgically implantable device of claim 17, in a form selected from the group consisting of vascular grafts, stents, electrical stimulation leads, heart valves, orthopedic devices, catheters, guide wires, shunts, sensors, replacement devices for nucleus pulposus, cochlear or middle ear implants, and intraocular lenses.

\* \* \* \* \*